United States Patent [19]

Dudley

[11] Patent Number: 4,639,246
[45] Date of Patent: Jan. 27, 1987

[54] CATHETER
[75] Inventor: Ralph S. Dudley, Anaheim, Calif.
[73] Assignee: Animal Healthcare Products, Vernon, Calif.
[21] Appl. No.: 773,569
[22] Filed: Sep. 9, 1985
[51] Int. Cl.⁴ .................. A61M 5/00; A61M 25/00
[52] U.S. Cl. .................. 604/158; 604/280; 122/207.14
[58] Field of Search .......... 604/280, 158–163, 604/264; 122/207.14, 200.26, 305.3

[56] References Cited
U.S. PATENT DOCUMENTS

| 2,116,083 | 5/1938 | Rusch | 604/280 X |
| 2,230,218 | 2/1941 | Asche | 604/43 |
| 3,064,653 | 11/1962 | Coanda . | |
| 3,190,290 | 6/1965 | Alley et al. | 604/280 |
| 3,295,527 | 1/1966 | Alley et al. . | |
| 3,828,767 | 8/1974 | Spiroff et al. . | |
| 3,885,561 | 5/1975 | Cami . | |
| 3,890,976 | 6/1975 | Bazell et al. . | |
| 4,143,658 | 3/1979 | Rambosek | 128/207.14 X |
| 4,275,724 | 6/1981 | Behrstock . | |
| 4,381,011 | 4/1983 | Somers, III | 604/280 X |
| 4,391,276 | 7/1983 | Lazarus et al. | 604/266 |
| 4,445,897 | 5/1984 | Ekbladh et al. . | |
| 4,465,482 | 8/1984 | Mainz . | |

FOREIGN PATENT DOCUMENTS
3325972 1/1972 U.S.S.R. .................. 604/280

Primary Examiner—Stephen C. Pellegrino
Attorney, Agent, or Firm—William W. Haefliger

[57] ABSTRACT

A catheter is usable with a hollow needle insertable into an animal. The catheter plastic tube has axially elongated openings formed in its side, at locations which are spaced apart axially and spaced about the tube axis. Each opening has width at least about as great as the tube inner diameter, and the openings, when viewed sidewardly in widthwise direction have elongated U-shaped profile.

11 Claims, 4 Drawing Figures

U.S. Patent     Jan. 27, 1987     4,639,246
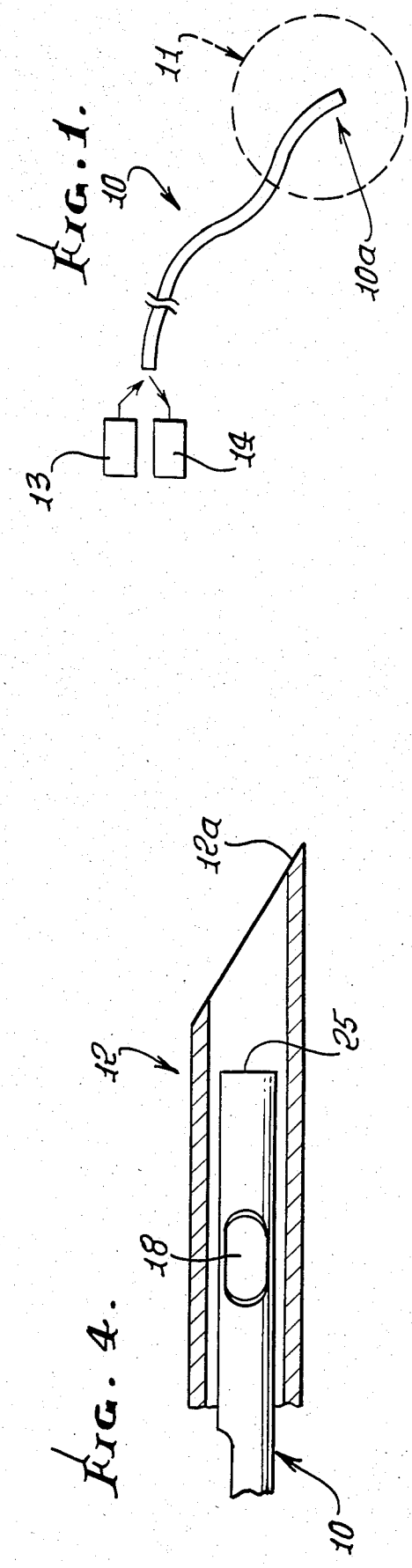
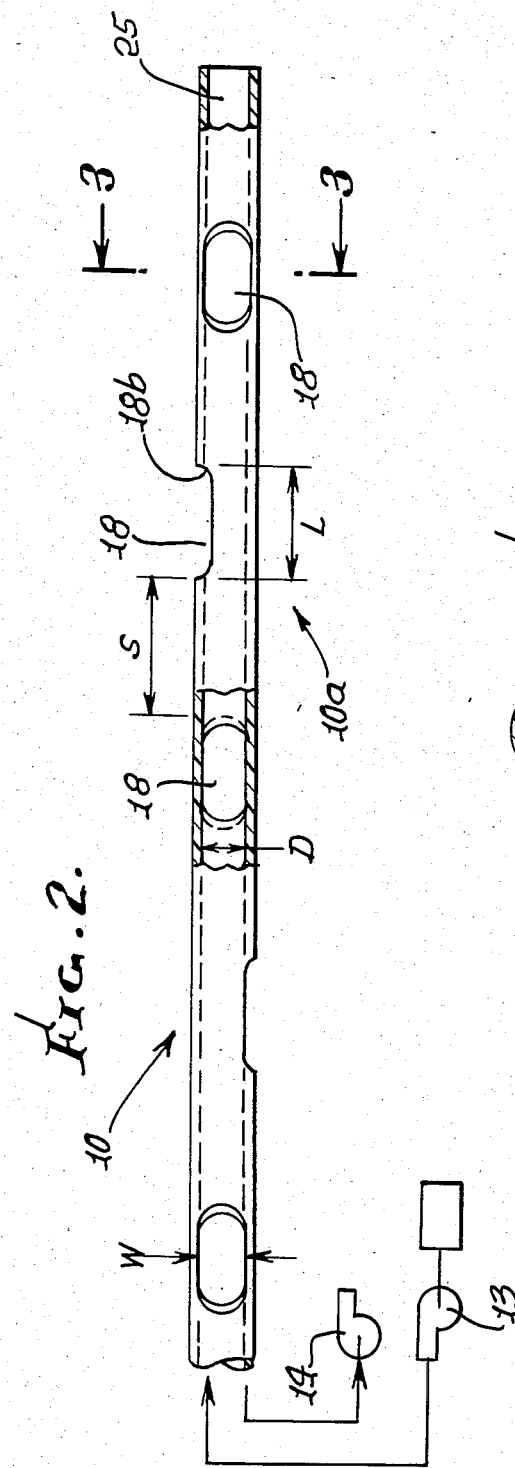
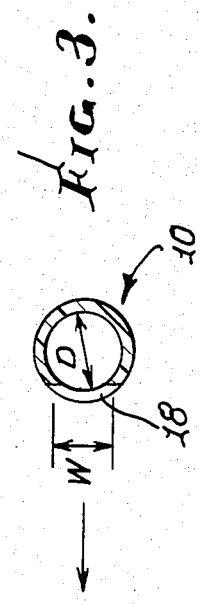

CATHETER

BACKGROUND OF THE INVENTION

This invention relates generally to catheters, and more particularly to the construction of catheters usable for veterinary purposes.

Flexible, plastic catheters of small diameter are easily sidewardly collapsible and side openings therein are small and tend to be easily plugged, in use, as by animal tissue or substances in animal vessels. There is a need for flexible catheters that minimize the risk of plugging, or flow stoppage.

SUMMARY OF THE INVENTION

It is a major object of the invention to provide an improved catheter overcoming the above problems, and also providing unusual advantages in construction, mode of operation and results, as for example when introduced into the trachea of an animal, such as a horse, dog and cat.

Basically the catheter comprises:

(a) an elongated, flexible plastic tube sized to pass lengthwise through a needle and to be threaded through the needle after its insertion into the animal trachea, (b) said tube having an end portion adapted to extend into the trachea, and at least four side openings in said end portion to deliver fluid to the trachea, and to withdraw fluid therefrom, (c) said openings spaced at different distances from the terminal of said end portion.

As will be seen, the openings are typically elongated in the direction of the tube, and have widths approximately equal to the inner diameter of the tubing; also, they are typically spirally located at different azimuths relative to a lengthwise axis defined by the tubing, and in the end portion of the tube of length less than 1½ inches. Further, the end of the tubing is preferably open, and there are about five of such spirally spaced, elongated side openings spaced apart so as not to weaken the tube, yet to provide for maximum flow, with concomitant very small risk of total flow cut-off.

These and other objects and advantages of the invention, as well as the details of an illustrative embodiment, will be more fully understood from the following specification and drawings in which:

DRAWING DESCRIPTION

FIG. 1 shows use of a catheter incorporating the invention;

FIG. 2 is a fragmentary side elevation, partly in section, showing a catheter incorporating the invention; and FIG. 3 is a section taken on lines 3—3 of FIG. 2; and FIG. 4 is a fragmentary side elevation, showing the catheter inserted in a needle to be inserted into a vessel in an animal.

DETAILED DESCRIPTION

In FIG. 1, a flexible catheter 10 is shown as arbitrarily curved corresponding to the vessel or other portion of the body 11 of an animal into which it is inserted. It comprises an elongated tube adapted to be relatively displaced, or threaded, axially through a tubular needle, as at 12 in FIG. 4, after insertion of the sharpened end 12a of the needle into a vessel of the animal, such as a trachea, for example. Thus, the catheter may be introduced into the vessel and fed to a local zone 11 to be treated, in the animal. FIG. 1 also shows means 13, such as a pump for example to introduce treatment fluid into the catheter, for flow to the animal zone 11 to be treated; and another means 14 such as a pump, to apply suction to the catheter, to withdraw fluid from zone 11.

The catheter tubing with unusual advantage consists of synthetic resin, such as polyurethane; its outer diameter is typically between 1/16 and 3/16 inches; and its gauge is typically between 16 and 12.

In accordance with an important aspect of the invention, the tube has end portion 10a less than about 1½ inches in length, and wherein at least four fluid passing side openings 18 are formed, and preferably five or six such side openings are formed. Those openings are elongated in the lengthwise direction of the tubing, and its axis, to minimize the risk of their being totally clogged or plugged by adjacent tissue or obstructions in the animal, but without unduly weakening the tubing. This is best achieved by providing openings of a length L between 1 and 2 times the tubing outer diameter. Also, the openings have width W approximately equal to the inner diameter D of the tubing, as shown, so as not to close up should the flexible tubing partially collapse, radially, under suction pressure, or tissue pressure. As indicated, $L>>W$.

Also, to ensure against plugging of all openings, they are located in four quadrants, and at different azimuths relative to the tubing axis, as for example at 90°, 180°, 270°, 0° and 90°, in sequence along the tubing, as shown in FIG. 2. more generally the side openings are spaced apart spirally along and about the tubing. The axial spacing S of successive openings, along the axis, is between one and three times L.

Finally, the tubing is preferably open ended at 25.

Accordingly, the risk that all of the openings will simultaneously became unable to pass fluid flow, in use, as through local collapse of the end of the catheter, or external plugging of certain side openings, is reduced almost to nil; the flexible catheter maintains its bending strength due to axial spacing of the elongated openings (i.e. the elongated openings are not so close together as to unduly weaken the catheter). Therefore, the utility and safety of the catheter are optimized.

Note that the end walls 18b of the openings are beveled, or angled as shown so as not to form sharp corners in which material could build up.

I claim:

1. For use with a hollow needle insertible into the trachea of an animal, the improvement comprising
   (a) an elongated, flexible plastic tube sized to pass lengthwise through the needle and to be threaded through the needle after its insertion into the animal trachea,
   (b) said tube having an end portion adapted to extend into the trachea and at least four side openings in said end portion to deliver fluid to the trachea, and to withdraw fluid therefrom,
   (c) said openings spaced at different distances from the terminal of said end portion, said openings being elongated in the direction of the tube, the lengths of said elongated openings being at least as great as the tube diameter, the openings' widths approximately equal to the inner diameter of the tube,
   (d) each opening being symmetrical with respect to a tube axial radial plane bisecting that opening, the opening profile, viewed normal to said plane having elongated U-shape, with an elongated base the depth of which is greater than the tubing wall thickness, (e) the widths of the openings being constant along major lengths of the openings.

2. For use with a hollow needle insertible into the trachea of an animal, the improvement comprising (a) an elongated, flexible plastic tube sized to pass lengthwise through the needle and to be threaded through the needle after its insertion into the animal trachea, (b) said tube having an end portion adapted to extend into the trachea and at least four side openings in said end portion to deliver fluid to the trachea, and to withdraw fluid therefrom, (c) said openings spaced at different distances from the terminal of said end portion, (d) said openings being elongated in the direction of the tube, and the lengths of said elongated openings being at least as great as the tube diameter, (e) the openings haing constant widths along their elongated lengths, at least about as great as the inner diameter of the tubing, the depth of said openings along major lengths thereof exceeding the tubing wall thickness.

3. The improvement of claim 1 wherein said openings are spirally located at different azimuths relative to a length-wise axis defined by the tubing.

4. The improvement of claim 1 wherein said openings are located in said tubing end portion the length of which, from the tubing terminal, is less than about 1½ inches.

5. The improvement of claim 1 wherein the openings are spaced apart axially of the tubing at distances between one and three times the openings lengths.

6. The improvement of any of claims 1-4 wherein the tubing is open ended, at said terminal.

7. The improvement of claim 1 wherein the tubing consists of polyurethane, and is between 1/16 and 3/16 inches in diameter.

8. The improvement of any one of claims 1-5 including said needle through which the tubing extends.

9. The improvement of claim 1 wherein there are five of said side openings, and the tubing is open ended, at said terminal.

10. For use with a hollow needle insertible into the treachea of an animal, the improvement comprising (a) an elongated, flexible plastic tube sized to pass lengthwise through the needle and to be threaded through the needle after its insertion into the animal, (b) said tube having an end portion containing at least four side openings spaced about an axis defined by the tubing, and spaced apart lengthwise of the tubing, (c) the openings being elongated lengthwise of the tubing, and having widths along their elongated lengths at least about as great as the inner diameter of the tubing, (d) each opening when viewed in a widthwise direction having a U-shaped profile with an elongated base and beveled opposite ends, the depth of the opening to said elongated base being greater than the tubing wall thickness, (e) the widths of said openings being constant along major lengths of the openings.

11. The improvement of claim 10 wherein the U-shaped profile of each opening has substantially constant depth along the base of the U and which is greater than the tube wall thickness.

* * * * *